United States Patent [19]

Kumaki

[11] Patent Number: 4,977,242
[45] Date of Patent: Dec. 11, 1990

[54] ULTRA FINE POLYMER PARTICLE, COMPOSITE MATERIAL THEREOF AND METHODS OF PREPARATION THEREOF

[75] Inventor: Jiro Kumaki, Tokyo, Japan

[73] Assignee: Research Development Corp. of Japan, Japan

[21] Appl. No.: 323,821

[22] Filed: Mar. 15, 1989

Related U.S. Application Data

[62] Division of Ser. No. 841,189, Mar. 19, 1986, Pat. No. 4,839,463.

[30] Foreign Application Priority Data

Apr. 1, 1985 [JP] Japan .................................. 60-66556

[51] Int. Cl.$^5$ ............................................... C08F 6/00
[52] U.S. Cl. ...................................... 528/499; 528/502
[58] Field of Search ............... 528/480, 483, 495, 497, 528/498, 499, 502

[56] References Cited

U.S. PATENT DOCUMENTS 4,452,976  6/1984  Kohyama ........................... 528/491
4,603,194  7/1986  Mendiratta ......................... 528/491

Primary Examiner—Christopher Henderson
Attorney, Agent, or Firm—Stephen F. K. Yee

[57] ABSTRACT

A cumulatable ultrafine polymer particle consisting of one molecular chain of the polymer is prepared by spreading a dilute solution of the polymer at the interface between the atmosphere and a subphase solution having a weak affinity for the polymer, and evaporating the spreading solvent or dissolving it into the subphase. A composite material comprising the polymer particles is produced by contacting the particles formed on the subphase solution with the surface of a substrate. The particles are cumulated on the substrate in a ratio of area occupied by the particles of at least 10%. The particles may be cumulated in multiple layers on the substrate.

11 Claims, 4 Drawing Sheets

EVAPORATION OR DISSOLVING OF THE SOLVENT
(REPETITION OF DROPPING, SPREADING AND EVAPORATION OR DISSOLVING)

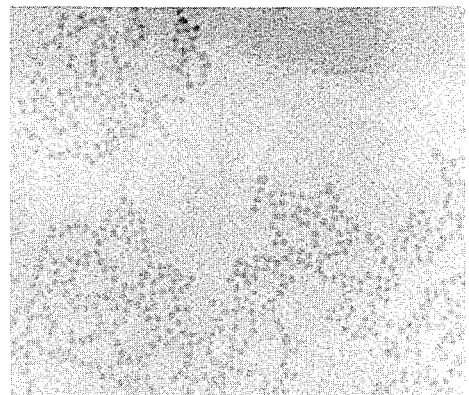
FIG. 2  3000Å
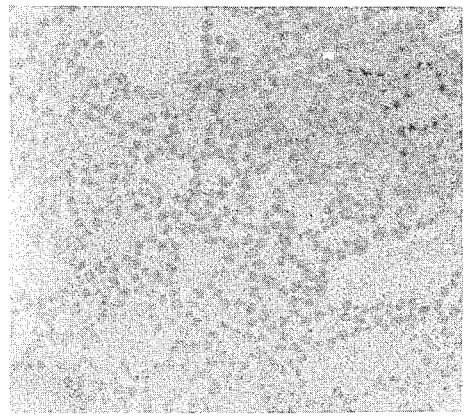
FIG. 3  3000Å

ULTRA FINE POLYMER PARTICLE, COMPOSITE MATERIAL THEREOF AND METHODS OF PREPARATION THEREOF

This application is a division of application Ser. No. 841,189, filed Mar. 19, 1986, now U.S. Pat. No. 4,839,463.

BACKGROUND OF THE INVENTION (1) Technical Field

The present invention relates to a cumulatable ultra fine polymer particle consisting of one molecular chain of a polymer, a composite material comprising the aforesaid cumulatable ultra fine polymer particles cumulated on a substrate in a ratio of area occupied with the ultra fine polymer particles of at least 10%, and method of preparation thereof.

(2) Background Information

According to the solution theory of polymers, the polymer exists in a dilute solution as isolated chains. The dilute solution is the solution having a concentration of not more than $C^*$ defined by the following formula.

$$C^* = 3M/(4\pi N_A <S^2>^{3/2})$$

where $C^*$ is the concentration, M is the molecular weight of the polymers, $\pi$ is the ratio of the circumference of a circle to its diameter, $N_A$ is the Avogadro number, and $<S^2>$ is the square mean of the radius of gyration of the polymer chain.

It has been considered that an ultra fine polymer particle consisting of one molecular chain of the polymer can probably be obtained by removing the solvent while maintaining the dispersion state of the polymer in the dilute solution.

However, it is very difficult to remove the solvent from the dilute solution while maintaining the molecular dispersion. The removal of the solvent under the usual conditions of the solvent casting process causes an increase of the concentration of the solution, finally resulting in association of the polymer molecules. For this reason, it is impossible to obtain an ultra fine polymer particle consisting of one molecular chain of the polymer by ordinary methods.

Although many useful applications are expected, almost no attempt has recently been made to obtain an ultra fine polymer particle consisting of one molecular chain of the polymer, because of this difficulty. Previously, some attempts were made. For example, M. J. Richardson, Proc. Roy. Sec. (London), A279, 50 (1964) reported the method for producing an ultra fine particle consisting of one polymer chain by spraying the dilute solution of the polymer in the mixed solvent onto a carbon vacuum-evaporated film and vaporizing the solvent therefrom. In this method, more volatile good solvent for the polymer and less volatile poor solvent were used in combination as the mixed solvent. It was reported that the composition was shifted to the poor solvent side during the vaporizing process of the solvent and the polymer became highly compressed conformation then became the ultra fine polymer particle. It was further described that the polymer widely spread on the substrate and an ultra fine polymer particle was not formed, when the dilute solution of the polymer in the good solvent alone was sprayed.

The ultra fine polymer particle consisting of one molecular chain of the polymer, prepared by the spray method described above, has the following disadvantages.

In the first place, the ultra fine polymer particle rigidly adheres to the substrate, because the dilute solution is sprayed on the solid substrate. Consequently, the ultra fine polymer particle thus obtained can not be cumulated on another substrate.

Secondly, it is impossible substantially to increase the ratio of area occupied with the particles, because a large amount of the solution sprayed on the solid substrate for increasing a ratio of area occupied with the particles causes association of the polymer chains. For this reason, the widely applicable structures such as the structure having the particles more densely packed and the structure having the particles cumulated in multi layers can not be obtained.

Further, R. F. Boyer et al, J. Appl. Phys., 16, 621 (1945) reported the summary of the paper presented by Kropa et al at Electron Microscope Society Meeting, New York City, Jan. 11-15, 1944 as follows:

"More recently Kropa, Burton, and Barnes have investigated films of polystyrene cast onto a water surface from solution in organic solvents. These films exhibited at various points black nodules whose size was in agreement with that predicted by the viscosity molecular weight of the polymers, if one assumed that the material in these nodules had the same bulk density as polystyrene. However, the method did not appear to work for all specimens, but only on certain high molecular weight polymers prepared in a special manner."

In this report, however, the details of the technical procedure and the obtained result are not disclosed. Therefore, the detailed informations are unknown.

SUMMARY OF THE INVENTION

The present inventor has variously studied the formation of ultra fine polymer particles from dilute solutions of polymers. As a result, a cumulatable ultra fine polymer particle has successfully been obtained, thus arriving at the present invention.

In accordance with the present invention, there are provided a cumulatable ultra fine polymer particle consisting of one molecular chain of a polymer; a composite material comprising ultra fine polymer particles each consisting of one molecular chain of the polymer cumulated on a substrate in a ratio of area occupied with the ultra fine polymer particles of at least 10%; a method for preparing the cumulatable ultra fine polymer particle consisting of one molecular chain of the polymer, which comprises spreading a dilute solution of the polymer at the interface between the air and a subphase solution which has a weak affinity for the polymer, and evaporating the spreading solvent or dissolving the spreading solvent into the subphase solution; a method for preparing the composite material comprising the cumulatable ultra fine polymer particles each consisting of one molecular chain of the polymer cumulated on the substrate, which comprises spreading the dilute solution of the polymer at the interface between the air and a subphase solution which has a weak affinity for the polymer, evaporating the spreading solvent or dissolving the spreading solvent into the subphase solution, thereby producing the ultra fine polymer particles each consisting of one molecular chain of the polymer on the subphase solution, and transferring the ultra fine polymer particles onto the substrate by bringing the substrate into contact with the subphase surface; and a method for preparing the composite material comprising built-up multilayers of ultra fine polymer particles each consisting of one molecular chain of the polymer cumulated on the substrate, which comprises further bringing the above obtained composite material into contact with the ultra fine polymer particles formed on the subphase surface, and cumulating the ultra fine polymer particles thereon in multilayers.

As used herein, the term "subphase" has the same meaning as the same technical term is commonly used and understood in the literature relating to methods for forming a monolayer film on an aqueous medium, or "phase", such as the Langmuir-Brodgett method, and refers to a liquid.

In general, the conventional ultra fine polymer particle consists of many molecular chains of the polymer. However, the ultra fine polymer particle of the present invention substantially consists of one molecular chain of the polymer.

The ultra fine polymer particle may take any shape such as a spherical, spheroidal or cylindrical shape.

The size of the ultra fine polymer particle may largely vary from 10 Å to 1,000 Å, depending on its molecular weight.

As the substrate used in the present invention, there can be mentioned, for example, a metal plate such as a chrome plate, a plastic plate such as a polystyrene or polymethyl methacrylate plate, a glass plate, a calcium fluoride plate, a silicon single crystal plate, a carbon reinforced collodion membrane and the like. The substrate is not necessarily platelike in shape, but it may be spherical, cylindrical and so on in shape.

The term 'cumulate' means to place the formed ultra fine polymer particles on the substrate in one or more layers.

The ratio of area occupied with the ultra fine polymer particles is defined by the ratio of area occupied with the ultra fine polymer particles in a square, a side of which is at least 50 times the average size of the ultra fine polymer particles in length. The square is so determined that the ratio of area occupied with the ultra fine polymer particles becomes highest. The ratio of area occupied with the ultra fine polymer particles can be 10% or more, preferably 20% or more, and further preferably 100% or more.

The cumulatable ultra fine polymer particle consisting of one molecular chain of the polymer of the present invention can be obtained, for example, by spreading the dilute solution of the polymer at the interface between the atmosphere and the subphase solution such as water, an organic solvent or mercury, and evaporating the spreading solvent or dissolving the spreading solvent into the subphase solution.

In the case of the subphase solution having a weak affinity for the polymer, the molecular chains of the polymer monomolecularly aggregate without being largely spread on the subphase solution, then the ultra fine polymer particles consisting of one molecular chain of the polymer of the present invention is easily obtained. Therefore, the subphase solution is preferable to have a weak affinity for the polymer.

That is to say, there can be mentioned (1) a combination of a spreading solution comprising a polymer having a weak affinity for water and the subphase of water or an aqueous solution, and (2) a combination of a spreading solution comprising a hydrophilic polymer and the subphase solvent having a weak affinity for the polymer.

When water or an aqueous solution is used as the subphase, a polymer having a weak affinity for water or an aqueous solution is used.

The polymer having a weak affinity for water or an aqueous solution includes, for example, alkylene polymers such as polyethylene and polypropylene, diene polymers such as polybutadiene and polyisoprene, polyvinyl halides such as polyvinyl chloride, polyvinylidene chloride, polyvinyl fluoride and polyvinylidene fluoride, and styrene derivatives such as polystyrene and poly-α-methylstyrene.

Further, random copolymers, block copolymers and graft copolymers of the polymers described above, and also mixture thereof can be used. Particularly, polystyrene and polyvinyl chloride is preperably used.

As the spreading solvent, a solvent which thinly spreads without gathering in the form of a lens when dropped on the water surface is desirable. There are usually used chloroform, hexane, ethanol, benzene and the like, alone or as mixtures thereof. Each of the spreading solvents is preferred to be transferred into the gas or liquid phase not to remain on the interface.

The concentration of the polymer in the spreading solvent is required to be lower than $C^*$ previously described. The lower than $C^*$ the concentration is, the better result is obtained. At a concentration slightly lower than $C^*$, floating matter of the polymer is observed on the water surface. When the concentration is not sufficiently dilute, the ultra fine polymer particle obtained includes one or more molecular chain. It becomes feasible to obtain only the ultra fine polymer particles consisting of one molecular chain of the polymer by further decreasing the concentration. This critical concentration is decided according to the kinds of polymers, spreading solvents and liquids for the subphase, spreading conditions and the like.

As readily presumed from the above description, the control of the concentration will make it possible to prepare the particle containing more than one molecular chain. In this case, however, there exists a distribution of the molecular chains contained in the particle.

Water used for the subphase is preferable not to include any surface-active impurities. Surface-active impurities in water change the properties of the water surface to influence the shape of the particle produced. Instead of water, aqueous solutions of inorganic compounds, organic compounds and the like can be used.

As the inorganic compound used in the aqueous solution for the subphase, there can be mentioned, for example, salts such as barium chloride, calcium chloride, potassium chloride, potassium sulfate, potassium hydroxide, magnesium sulfate, sodium chloride, sodium bromide, sodium nitrate, sodium hydroxide, lead chloride, lead acetate, ferric chloride, and cadmium chloride, acids such as hydrochloric acid, nitric acid and sulfuric acid, ammonium sulfate and the like.

The organic compound used in the aqueous solution for the subphase includes acetonitrile, acetone, aminobenzoic acid, ethanol, formic acid, glycerin, dioxane, phenol, butanol, propanol, propionic acid, acetic acid, methanol and the like.

On the other hand, as the polymer having a strong affinity for water or the aqueous solution, there can be mentioned, for example, a polymer consisting of an ester of acrylic acid and a lower molecular alcohol such as polymethyl acrylate or polyethyl acrylate, a polymer consisting of an ester of methacrylic acid and a lower molecular alcohol such as polymethyl methacrylate or polyethyl methacrylate, a polymer consisting of a vinyl ether having a lower fatty chain such as polymethyl vinyl ether or polyethyl vinyl ether, a polymer consisting of an amino acid such as poly-DL-α-aminolauric acid, poly-DL-alanine or polyleucine, polyvinyl alcohol, a derivative of polyvinyl alcohol and a lower aldehyde such as polyvinyl formal, polyvinyl acetal or polyvinyl butyral, polyvinyl acetate, and a derivative of polyvinyl acetate and a lower alcohol.

These polymers spread and do not aggregate on the surface of water or the aqueous solution, since they have a good affinity for water. Therefore, it is difficult to form ultra fine polymer particle. However, ultra fine polymer particles can be prepared from these polymers by using liquids having a poor affinity for the polymers as the liquid for the subphase. Though the various liquids are suitable for the polymers according to their properties, the liquids suitable for these polymers in common includes, for example, aliphatic compounds such as heptane, octane and the like, and liquids such as mercury and the like. Other than these liquids, the particular liquids suitable for the individual polymers can be used for the subphase. For example, in the case of polymethyl acrylate, there can be used ethyl ether, methanol, ethanol, carbon tetrachloride and the like. For polyethyl acrylate, there can be used solvents such as ethyl ether aliphatic alcohols having at least 5 carbon atoms, and cyclohexanol. For polymethyl methacrylate, there are suitably used methanol, ethylene glycol, buthylene glycol, ethers such as ethyl ether and isopropyl ether, carbon tetrachloride, formamide, cresol and the like. In the case of polyethyl methacrylate, there can be used methanol, ethylene glycol, isopropyl ether and the like. For polymethyl vinyl ether and polyethyl vinyl ether, there can be used ethylene glycol, ethyl ether and the like. For polyvinyl alcohol, there are suitable halogenated hydrocarbons, lower alcohols, tetrahydrofuran, dioxane, formalated ethylene glycol, ketones, carboxylic acids, esters and the like. In the case of polyvinyl formal, there can be used methanol, ethanol, dioxane, esters and the like. Ethyl ether and the like can be used for polyvinyl acetal. Methylene chloride, aliphatic ketones and the like are suitably used for polyvinyl butyral.

The composite material comprising the ultra fine polymer particles each consisting of one molecular chain of the polymer cumulated on the substrate is prepared, for example, by spreading the dilute solution of the polymer at the interface between the atmosphere and the subphase solution such as water, an organic solvent or mercury, evaporating the spreading solvent or dissolving it into the subphase, thereby producing the ultra fine polymer particles each consisting of one molecular chain of the polymer on the subphase solution, and transferring the ultra fine polymer particles onto the substrate by bringing the substrate into contact with the ultra fine polymer particles formed on the subphase. In this case, the ratio of area occupied with the ultra fine polymer particles can be varied by transferring the ultra fine polymer particles onto the substrate after collecting the ultra fine polymer particles formed on the liquid surface by means of moving barriers. Also, the composite material comprising the ultra fine polymer particles cumulated on the substrate in multilayers can be obtained by further bringing the substrate having the ultra fine polymer particles cumulated thereon into contact with the ultra fine polymer particles formed on the subphase. Thus, according to the method wherein the ultra fine polymer particles previously prepared on the liquid surface are cumulated on the substrate, the composite material of the ultra fine polymer particles having the ratio of area occupied with the ultra fine polymer particles of at least 10% can be obtained. On the other hand, this composite material has not been able to be produced by the conventional methods such as the spray method and the like wherein the ultra fine polymer particles are prepared on the substrate.

The heating of the ultra fine polymer particles obtained makes it possible to fuse the ultra fine polymer particles with each other, or the ultra fine polymer particles with the substrate.

As the substrate, there can be used a metal plate, a plastic plate, a glass plate, a calcium fluoride plate, a silicon single crystal plate, a carbon reinforced collodion membrane and the like as previously described.

BRIEF DESCRIPTION OF THE DRAWINGS

FIG. 2 is an electron microscopic photograph showing the ultra fine polymer particles of polystyrene having a weight average molecular weight of 3,840,000;

FIG. 3 is an electron microscopic photograph showing the ultra fine polymer particles of polystyrene having a weight average molecular weight of 8,420,000;

The present invention will now be described in detail with reference to the following examples that by no means limit the scope of the invention.

EXAMPLE 1

Commercially available monodisperse polystyrene was dissolved in benzene to make a solution having a concentration of about $2 \times 10^{-4}\%$ by weight. The concentration C* shows a value from about 0.1 to about 0.3% by weight in the molecular weight represented here, though C* depends on the molecular weight of the polymer.

As schematically illustrated in FIGS. 1a–1e, the solution was spread at the interface between the air and water by dropping a drop of the dilute solution on the surface of pure water in a container 10 using an injector 12 (FIG. 1a), permitting the drop of solution to completely spread on the water surface and evaporate (FIG. 1b), adding a new drop of the benzene solution (FIG. 1c), and repeating this process. Usually 20 cc of the solution was spread on the water surface having an area of 560 cm².

The sample for electron microscopic observation was prepared by bringing copper meshes for the electron microscope which were covered with a collodion membrane and reinforced with carbon into contact with the ultra fine polymer particles formed on the water surface in parallel thereto, and thereby transferring the particles onto the meshes.

In FIGS. 2 and 3, there are shown electron microscopic photographs of the ultra fine particles of polystyrene polymers having weight average molecular weights of 3,840,000 and 8,420,000, respectively. Number average diameters of the particles were 336 and 465 Å, respectively.

Figure 1A:
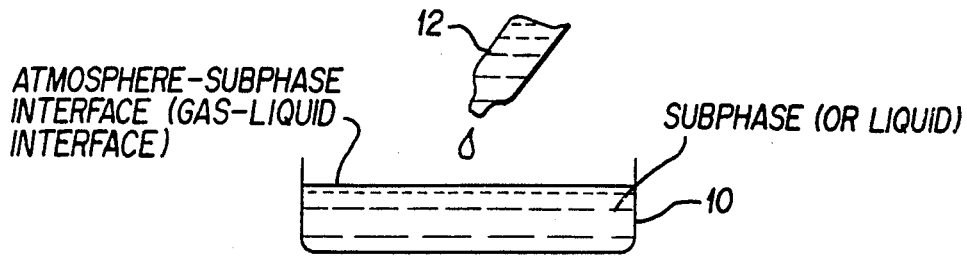
FIGS. 1a–1e schematically illustrate a technique for spreading a dilute solution of polymer on the surface of a subphase.
Figure 1B:
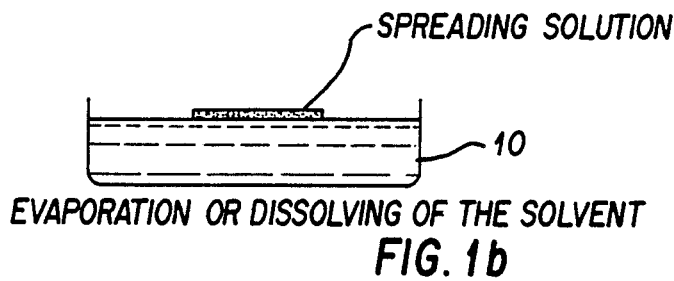
Figure 1C:
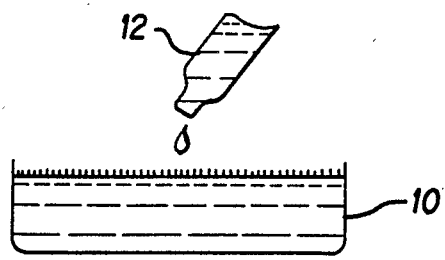
Figure 1D:
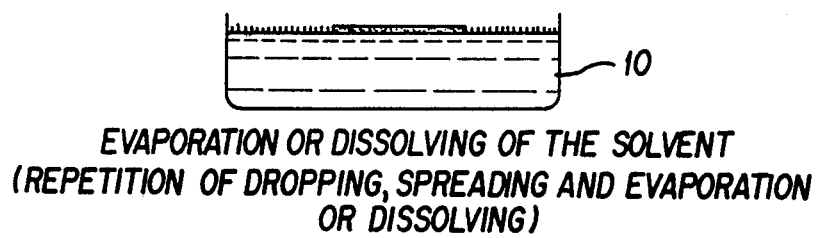
Figure 1E:
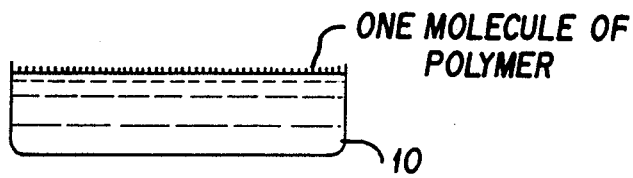
Figure 4:
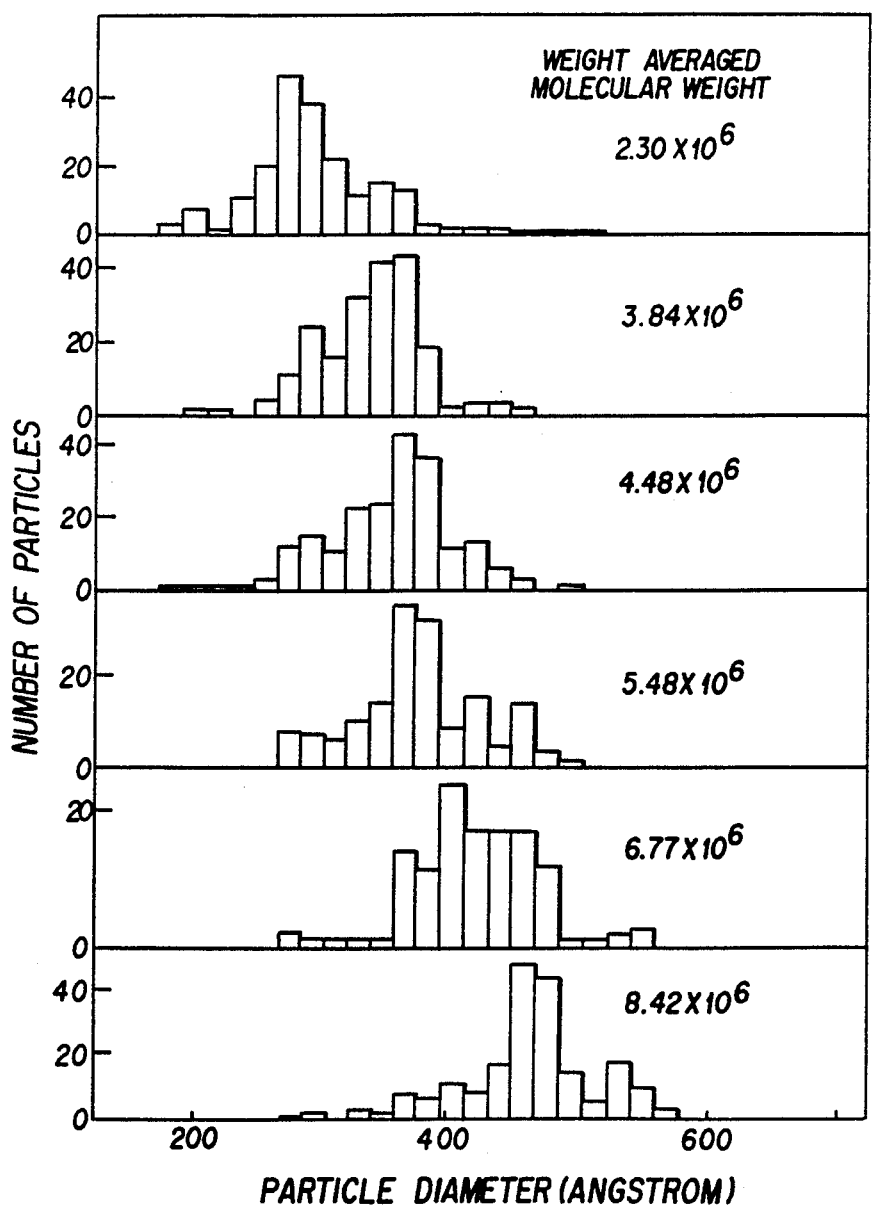
FIG. 4 is a graph showing the particle diameter distributions of polystyrene ultra fine particles of different weight average molecular weights.

FIG. 4 is a graph showing the particle size distributions of polystyrene polymers having weight average molecular weights of 2,300,000, 3,840,000, 4,480,000, 5,480,000, 6,770,000 and 8,420,000, respectively, in order from the top. Number average diameters of the particles are 295, 336, 351, 374, 418 and 465 Å, respectively, in order from the top. The size of the particle directly reflects molecular weight. According to the electron microscopic observations of these particles after being shadowed, the particles are found to be flat in shape.

EXAMPLE 2

Figure 5:
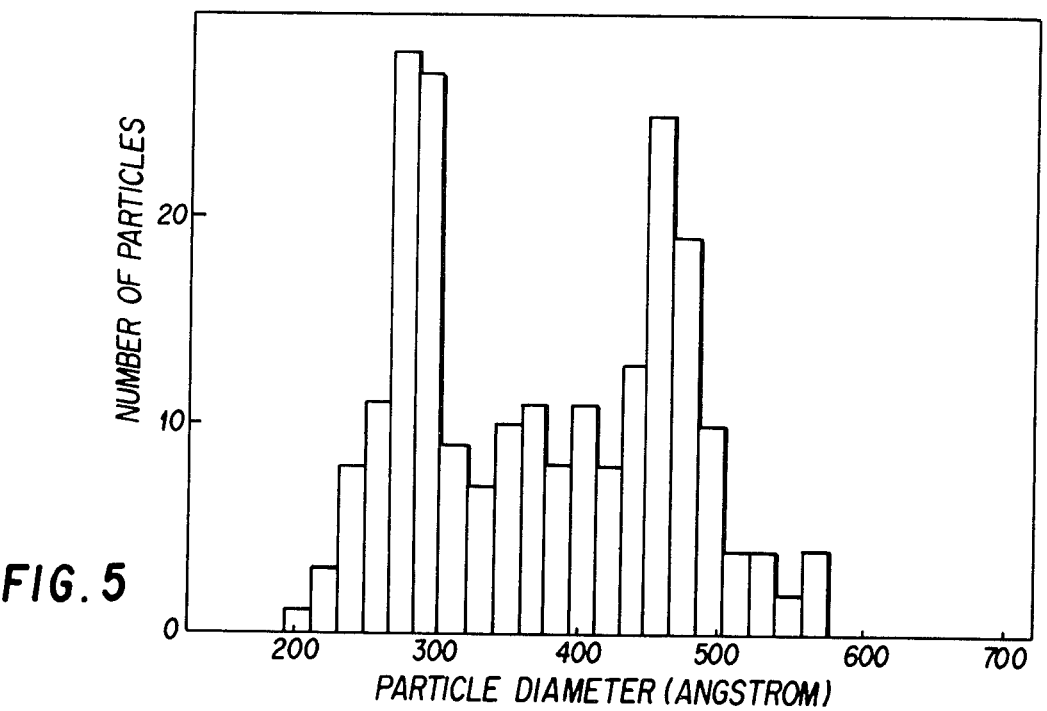
FIG. 5 is a graph showing the diameter distribution of the ultra fine particles obtained by spreading the mixture solution of two polystyrenes having different molecular weights.

A mixture of monodisperse polystyrene polymers having weight average molecular weights of 2,300,000 and 8,420,000, respectively, in a molar ratio of 1:1.3 was dissolved in benzene to make a benzene solution, which was spread in the same manner as that of Example 1. In FIG. 5, the particle diameter distribution of the particles thus obtained was shown. The particle diameter distribution exhibited two peaks, each of which agreed with that of the original polymers shown in FIG. 4. From this result, it is apparent the present ultra fine particle consists of one molecular chain of the polystyrene polymer.

With respect to the other polymers, except for polystyrene, having a weak affinity for water or an aqueous solution, the ultra fine polymer particle consisting of one molecular chain of the polymer was obtained in the same manner.

EXAMPLE 3

A solution of polystyrene having a weight average molecular weight of 3,840,000 was spread in the same manner as that of Example 1. The ultra fine polymer particles formed on the water surface were collected by means of moving barriers and then transferred onto the substrate by bringing a chrome plate into contact with the particles on the water surface in parallel thereto while compressing the particles at constant surface pressure. Thus, the composite material was obtained. When the particles were cumulated on the substrate in one layer at surface pressures of 1, 2, 5, 20 and 50 dyn/cm$^2$, there were obtained composite materials having ratios of area occupied with the particles of 11, 22, 40, 74 and 90% respectively. The ultra fine polymer particles cumulated on the chrome plate appeared as if fine powdery matter adhered thereto. It is considered that this results from the visible structure, because there are thick and thin portions in state of aggregation of the ultra fine polymer particles.

After compressing the ultra fine polymer particles on the water surface at constant surface pressure, the water surface was covered with a Teflon plate having a number of holes of such size as the substrate can enter therein, and the substrate was brought into contact with the water surface in the different holes, whereby the composite material comprising the ultra fine polymer particles cumulated in multi layers was obtained. The ultra fine polymer particles were cumulated at surface pressure of 20 dyn/cm in 5, 10, 30 and 50 layers. As the ultra fine polymer particles were cumulated in more layers, the surface of the substrate came to look more white. These composite material had a ratio of area occupied with the ultra fine polymer particles of more than 100%.

The composite materials of the ultra fine polymer particles were obtained, as was the case with the chrome plate, for a glass plate, a CaF$_2$ plate, a mica plate, a carbon reinforced collodion membrane and the like.

With respect to the other polymers, except for polystyrene, having a weak affinity for water or an aqueous solution, the composite material of the ultra fine polymer particles was obtained.

EXAMPLE 4

Using polystyrene having a weight average molecular weight of 3,840,000 as shown in FIG. 2, the same procedure as Example 1 was repeated, with the exception that the concentrations of the spreading solution were varied. This polymer has the concentration C* of 0.176% by weight.

Figure 6:
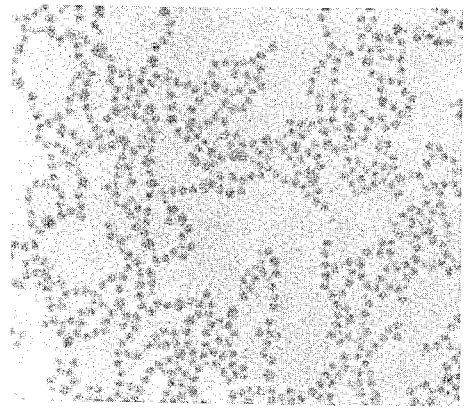
FIG. 6 is an electron microscopic photograph showing the ultra fine polymer particles spread from the dilute solution having a concentration of $2.30 \times 10^{-3}\%$ by weight.
Figure 7:
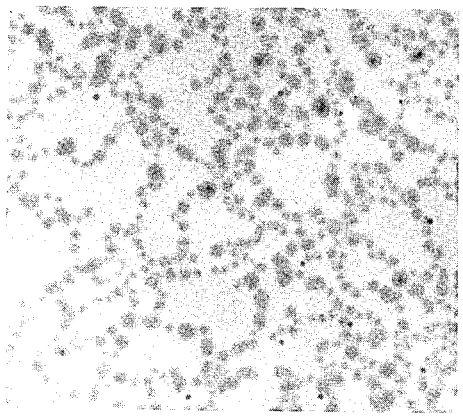
FIG. 7 is an electron microscopic photograph showing the ultra fine polymer particles spread from the dilute solution having a concentration of $2.33 \times 10^{-2}\%$ by weight.

In FIGS. 2, 6 and 7, there are shown the electron microscopic photographs of the ultra fine polymer particles prepared when spread from the solutions having concentrations of $2.29 \times 10^{-4}$, $2.30 \times 10^{-3}$ and $2.33 \times 10^{-2}$% by weight, respectively. With an increase in the concentration of the spreading solution, the ultra fine polymer particles contained particles of larger size, each of which was a ultra fine polymer particle consisting of two or more molecular chains of the polymer. In either concentration, there existed ultra fine polymer particles of smaller size and their size did not vary depending upon concentration. However, the proportion of the ultra fine polymer particles of smaller size increased with a decrease in concentration. From this result, it is proved that the ultra fine polymer particles of smaller size consists of one molecular chain of the polymer. For a concentration of $2.3 \times 10^{-3}$% by weight, the incorporation of the ultra fine polymer particles of larger size was observed. However, only the ultra fine polymer particles of smaller size were found for a concentration of $2.29 \times 10^{-4}$% of weight.

EXAMPLE 5

Polystyrene polymers having a weight average molecular weights of 600,000 and 950,000 were dissolved in benzene to prepare solutions having a concentration of about $2 \times 10^{-4}$% by weight. The solution was spread in the same manner as that of Example 1, and the obtained particles were similarly transferred onto the copper meshes for the electron microscope.

The decrease of the particles in size causes the difficulty of the particle observation by the electron microscope. Therefore, the particles were observed by the electron microscope after the particles were shadowed by the platinum-carbon simultaneous shadowing method.

Both samples had the similar ultra fine particle structure as shown in FIGS. 1 and 2. Number average diameters of the particles obtained from the polymers were 210 and 250 Å respectively, and the apparent dependence on molecular weight was observed.

It became apparent that the ultra fine particles were obtained even from the polymer having a molecular weight of several hundred thousand.

EFFECTS OF THE INVENTION

The cumulatable ultra fine polymer particle consisting of one molecular chain of the polymer of the present invention has advantages as will be described below.

The particle size and the particle size distribution can be precisely controlled by adjusting the molecular weight and the molecular weight distribution.

Further, there can be prepared the ultra fine polymer particle having a size of less than several hundred angstroms, which has conventionally been difficult to be prepared.

Furthermore, the particles can be densely packed by compressing the particles on the liquid surface by means of moving barriers, because the particles can be floated on the liquid surface. The particles on the liquid surface can be transferred or cumulated on the substrate.

The composite material comprising the ultra fine polymer particles each consisting of one molecular chain of the polymer and cumulated on the substrate in a ratio of area occupied with the ultra fine polymer particles of at least 10%, which is provided according to the present invention, has advantages as will be described below.

The ultra fine polymer particles of the present invention are not more than several hundreds angstroms in thickness. Therefore, they are applicable to a spacer for controlling a distance between substrates in an accuracy of about 100 Å by interposing them between the smooth substances. When a ratio of area occupied with the ultra fine polymer particles is less than 10%, the number of the particles are too small to obtain a sufficient strength. However, a ratio of area occupied with the ultra fine polymer particles of at least 10% makes it possible to increase a strength of the spacer.

This composite material can have a highly fine structure, because it is comprised of the particles having a size of less than several hundred of angstroms. For example, the composite material comprising the densely packed ultra fine polymer particles cumulated on the substrate is applicable as separation membranes, because of fine voids existing among the particles.

Further, there can be prepared the membrane having a highly fine structure and being similar to the micro phase separation structure of a block copolymer by densely cumulating on the substrate the ultra fine polymer particles consisting of two kinds of polymers which are insoluble in each other in a solid state. The membrane thus obtained can be used, for example, for antithrombogenic materials for which block copolymers have been used.

What is claimed is:

1. A method for preparing a composite material comprising cumulatable ultra fine polymer particles each consisting of one molecular chain of the polymer cumulated on a substrate, which comprises the steps:

spreading a dilute solution of the polymer on the surface of a subphase which has a weak affinity for the polymer.

evaporating the spreading solvent or dissolving the solvent into the subphase, thereby producing the ultra fine polymer particles each consisting of one molecular chain of the polymer on the subphase, and transferring the ultra fine polymer particles onto the substrate by bringing the substrate into contact with the ultra fine polymer particles formed on the subphase, the dilute solution of the polymer having a concentration of not more than C* represented by the formula:

$$C^* = 3M/(4\pi N_A <S^2>^{3/2})$$

where C* is the concentration, M is the molecular weight of the polymer, $\pi$ is the ratio of the circumference of a circle to its diameter, $N_A$ is the Avogadro number, and $S^2$ is the square mean of the radius of gyration of the polymer chain.

2. A method for preparing a composite material according to claim 1, wherein the subphase consists of water or an aqueous solution.

3. A method for preparing a composite material according to claim 1, wherein the spreading solvent is benzene.

4. A method for preparing a composite material according to claim 2, wherein the spreading solvent is benzene.

5. A method for preparing a composite material according to claim 1, wherein the polymer has a weak affinity for water or an aqueous solution.

6. A method for preparing a composite material according to claim 1, wherein the polymer is selected from a group consisting of a alkylene polymers, diene polymers, polyvinyl halides, styrene derivatives and random copolymers, block copolymers, graft copolymers and mixtures thereof.

7. A method for preparing a composite material according to claim 6, wherein the alkylene polymer is polyethylene or polypropylene.

8. A method for preparing a composite material method according to claim 6, wherein the diene polymer is polybutadiene or polyisoprene.

9. A method for preparing a composite material method according to claim 6, wherein the polyvinyl halide is polyvinyl chloride or polyvinylidene chloride.

10. A method for preparing a composite material method according to claim 6, wherein the styrene derivative is polystyrene or poly-$\alpha$-methylstyrene.

11. A method for preparing a composite material according to claim 1, further comprising cumulating the ultrafine polymer particles on said substrate in multiple layers by further contacting said substrate with the ultrafine polymer particles formed on the subphase for each layer cumulated.

* * * * *